(12) United States Patent
Winslow et al.

(10) Patent No.: US 7,335,203 B2
(45) Date of Patent: Feb. 26, 2008

(54) SYSTEM AND METHOD FOR IMMOBILIZING ADJACENT SPINOUS PROCESSES

(75) Inventors: Charles J. Winslow, Walnut Creek, CA (US); David Bohrer, Barrington, RI (US); Henry A. Klyce, Piedmont, CA (US)

(73) Assignee: Kyphon Inc., Sunnyvale, CA (US)

( * ) Notice: Subject to any disclaimer, the term of this patent is extended or adjusted under 35 U.S.C. 154(b) by 381 days.

(21) Appl. No.: 10/774,664

(22) Filed: Feb. 9, 2004

(65) Prior Publication Data

US 2004/0249379 A1    Dec. 9, 2004

Related U.S. Application Data

(60) Provisional application No. 60/446,868, filed on Feb. 12, 2003.

(51) Int. Cl.
 *A61B 17/56* (2006.01)
(52) U.S. Cl. .............................. 606/61; 606/70; 606/71
(58) Field of Classification Search ............ 606/69–71, 606/61
 See application file for complete search history.

(56) References Cited

U.S. PATENT DOCUMENTS

| | | | |
|---|---|---|---|
| 2,456,806 A | 12/1948 | Wolffe | |
| 2,677,369 A | 5/1954 | Knowles | |
| 3,426,364 A | 2/1969 | Lumb | |
| 3,648,691 A | 3/1972 | Lumb et al. | |
| 3,867,728 A | 2/1975 | Stubstad et al. | |
| 3,875,595 A | 4/1975 | Froning | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,479,491 A | 10/1984 | Martin | |
| 4,501,269 A | 2/1985 | Bagby | |
| 4,553,273 A | 11/1985 | Wu | |
| 4,554,914 A | 11/1985 | Kapp et al. | |

(Continued)

FOREIGN PATENT DOCUMENTS

CA        2015507        1/1991

(Continued)

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819-1825, © 1997, Lippincott-Raven Publishers.

(Continued)

*Primary Examiner*—Eduardo C. Robert
*Assistant Examiner*—James L Swiger
(74) *Attorney, Agent, or Firm*—Coats and Bennett PLLC

(57) ABSTRACT

A system and method for immobilizing adjacent spinous processes in accordance with the present invention can supplement primary fusion devices and methods by immobilizing spinous processes while bone from adjacent vertebral bodies grows together. The system requires less extensive surgical procedures than other common supplemental devices, and preferably does not require bone or ligament removal. One such system comprises three spacers positioned between spinous processes and adjustably connected with a plate positioned on either side of the spinous processes. Each plate includes grips, with each grip positioned adjacent to the spinous process, forming a clamp with a grip connected with the opposing plate.

10 Claims, 5 Drawing Sheets

U.S. PATENT DOCUMENTS

| | | |
|---|---|---|
| 4,599,084 A | 7/1986 | Nashef |
| 4,599,086 A | 7/1986 | Doty |
| 4,604,995 A | 8/1986 | Stephens et al. |
| 4,611,582 A * | 9/1986 | Duff .......................... 606/61 |
| 4,636,217 A | 1/1987 | Ogilvie et al. |
| 4,643,178 A | 2/1987 | Nastari et al. |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,772,287 A | 9/1988 | Ray et al. |
| 4,790,303 A | 12/1988 | Steffee |
| 4,834,757 A | 5/1989 | Brantigan |
| 4,878,915 A | 11/1989 | Brantigan |
| 4,904,260 A | 2/1990 | Ray et al. |
| 4,904,261 A | 2/1990 | Dove et al. |
| 4,913,134 A | 4/1990 | Luque |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 5,011,484 A | 4/1991 | Breard |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,084,049 A | 1/1992 | Asher et al. |
| 5,092,866 A | 3/1992 | Breard et al. |
| 5,122,130 A | 6/1992 | Keller |
| 5,123,926 A | 6/1992 | Pisharodi |
| 5,167,662 A | 12/1992 | Hayes et al. |
| 5,171,279 A * | 12/1992 | Mathews .................... 128/898 |
| 5,180,381 A | 1/1993 | Aust et al. |
| 5,192,327 A | 3/1993 | Brantigan |
| 5,258,031 A | 11/1993 | Salib et al. |
| 5,263,953 A | 11/1993 | Bagby |
| 5,290,312 A | 3/1994 | Kojimoto et al. |
| 5,304,178 A | 4/1994 | Stahurski |
| 5,306,309 A | 4/1994 | Wagner et al. |
| 5,352,225 A | 10/1994 | Yuan et al. |
| 5,387,213 A | 2/1995 | Breard et al. |
| 5,390,683 A | 2/1995 | Pisharodi |
| 5,395,372 A | 3/1995 | Holt et al. |
| 5,415,661 A | 5/1995 | Holmes |
| 5,443,514 A | 8/1995 | Steffee |
| 5,454,812 A | 10/1995 | Lin |
| 5,456,722 A | 10/1995 | McLeod et al. |
| 5,458,638 A | 10/1995 | Kuslich et al. |
| 5,458,641 A | 10/1995 | Ramirez Jimenez |
| 5,458,643 A | 10/1995 | Oka et al. |
| 5,470,333 A | 11/1995 | Ray |
| 5,496,318 A | 3/1996 | Howland et al. |
| 5,505,732 A | 4/1996 | Michelson |
| 5,514,180 A | 5/1996 | Heggeness et al. |
| 5,527,312 A | 6/1996 | Ray |
| 5,534,028 A | 7/1996 | Bao et al. |
| 5,534,029 A | 7/1996 | Shima |
| 5,540,689 A | 7/1996 | Sanders et al. |
| 5,549,679 A | 8/1996 | Kuslich |
| 5,554,191 A | 9/1996 | Lahille et al. |
| 5,562,736 A | 10/1996 | Ray et al. |
| 5,593,409 A | 1/1997 | Michelson |
| 5,609,634 A | 3/1997 | Voydeville |
| 5,645,597 A | 7/1997 | Krapiva |
| 5,645,599 A | 7/1997 | Samani |
| 5,653,761 A | 8/1997 | Pisharodi |
| 5,658,286 A | 8/1997 | Sava |
| 5,674,295 A | 10/1997 | Ray et al. |
| 5,674,296 A | 10/1997 | Bryan et al. |
| 5,676,702 A | 10/1997 | Ratron |
| 5,702,455 A | 12/1997 | Saggar |
| 5,725,582 A | 3/1998 | Bevan et al. |
| 5,766,252 A | 6/1998 | Henry et al. |
| 5,800,438 A | 9/1998 | Tuke et al. |
| 5,824,098 A | 10/1998 | Stein |
| 5,865,846 A | 2/1999 | Bryan et al. |
| 5,885,299 A | 3/1999 | Winslow |
| 5,888,224 A | 3/1999 | Beckers et al. |
| 5,888,226 A | 3/1999 | Rogozinski |
| 5,976,186 A | 11/1999 | Bao et al. |
| 6,001,130 A | 12/1999 | Bryan et al. |
| 6,022,376 A | 2/2000 | Assell et al. |
| 6,045,552 A | 4/2000 | Zucherman |
| 6,048,342 A | 4/2000 | Zucherman |
| 6,068,630 A | 5/2000 | Zucherman |
| 6,074,390 A | 6/2000 | Zucherman |
| 6,090,112 A | 7/2000 | Zucherman |
| 6,113,639 A | 9/2000 | Ray et al. |
| 6,149,652 A | 11/2000 | Zucherman |
| 6,152,926 A | 11/2000 | Zucherman |
| 6,156,038 A | 12/2000 | Zucherman |
| 6,156,067 A | 12/2000 | Bryan et al. |
| 6,183,471 B1 | 2/2001 | Zucherman |
| 6,190,387 B1 | 2/2001 | Zucherman |
| 6,190,414 B1 | 2/2001 | Young et al. |
| 6,234,705 B1 | 5/2001 | Troxell |
| 6,235,030 B1 | 5/2001 | Zucherman |
| 6,238,397 B1 | 5/2001 | Zucherman |
| 6,261,296 B1 | 7/2001 | Aebi et al. |
| 6,280,444 B1 | 8/2001 | Zucherman |
| 6,332,882 B1 | 12/2001 | Zucherman |
| 6,332,883 B1 | 12/2001 | Zucherman |
| 6,364,883 B1 * | 4/2002 | Santilli ........................ 606/69 |
| 6,368,351 B1 | 4/2002 | Glenn et al. |
| 6,371,984 B1 | 4/2002 | Van Dyke |
| 6,379,355 B1 | 4/2002 | Zucherman |
| 6,416,776 B1 | 7/2002 | Shamie |
| 6,419,676 B1 | 7/2002 | Zucherman |
| 6,419,677 B2 | 7/2002 | Zucherman |
| 6,436,145 B1 | 8/2002 | Miller |
| 6,440,169 B1 | 8/2002 | Elberg |
| 6,451,019 B1 | 9/2002 | Zucherman |
| 6,451,020 B1 | 9/2002 | Zucherman |
| 6,458,131 B1 | 10/2002 | Ray |
| 6,478,796 B2 | 11/2002 | Zucherman |
| 6,500,178 B2 | 12/2002 | Zucherman |
| 6,514,256 B2 | 2/2003 | Zucherman |
| 6,565,570 B2 | 5/2003 | Sterett et al. |
| 6,565,605 B2 | 5/2003 | Goble et al. |
| 6,582,433 B2 | 6/2003 | Yun |
| 6,582,437 B2 | 6/2003 | Dorchak |
| 6,626,944 B1 | 9/2003 | Taylor |
| 6,641,585 B2 | 11/2003 | Sato et al. |
| 6,652,527 B2 | 11/2003 | Zucherman |
| 6,652,534 B2 | 11/2003 | Zucherman |
| 6,695,842 B2 | 2/2004 | Zucherman |
| 6,699,246 B2 | 3/2004 | Zucherman |
| 6,699,247 B2 | 3/2004 | Zucherman |
| 6,712,819 B2 | 3/2004 | Zucherman |
| 6,746,485 B1 | 6/2004 | Zucherman |
| 6,755,841 B2 | 6/2004 | Fraser |
| 6,764,491 B2 | 7/2004 | Frey et al. |
| 6,770,095 B2 | 8/2004 | Grinberg |
| 6,796,983 B1 | 9/2004 | Zucherman |
| 6,902,566 B2 | 6/2005 | Zucherman |
| 6,926,728 B2 | 8/2005 | Zucherman et al. |
| 2001/0012938 A1 | 8/2001 | Zucherman |
| 2002/0029039 A1 * | 3/2002 | Zucherman et al. .......... 606/61 |
| 2004/0106998 A1 | 6/2004 | Ferree |

| | | | |
|---|---|---|---|
| 2004/0138750 A1 | 7/2004 | Mitchell | |
| 2004/0143332 A1 | 7/2004 | Krueger | |

FOREIGN PATENT DOCUMENTS

| | | |
|---|---|---|
| DE | 2821678 A1 | 4/1980 |
| DE | 3113142 A1 | 1/1982 |
| EP | 140790 A2 | 10/1984 |
| EP | 146347 A1 | 12/1984 |
| EP | 322334 A1 | 12/1988 |
| EP | 0677277 A2 | 10/1995 |
| EP | 0767636 B1 | 4/1997 |
| EP | 1138268 A1 | 10/2001 |
| FR | 2681525 A1 | 3/1993 |
| FR | 2705227 | 11/1994 |
| FR | 2707864 A1 | 1/1995 |
| FR | 2717675 | 9/1995 |
| FR | 2722088 | 1/1996 |
| FR | 2722980 A1 | 2/1996 |
| FR | 2724554 | 3/1996 |
| FR | 2780269 A1 | 12/1999 |
| FR | 2782911 A1 | 3/2000 |
| FR | 2806614 A1 | 9/2001 |
| FR | 2806616 A1 | 9/2001 |
| GB | 780652 | 8/1957 |
| SU | 1484348 A1 | 6/1989 |
| WO | WO 90/00037 | 1/1990 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |
| WO | WO 02/051326 | 7/2002 |

OTHER PUBLICATIONS

Waldemar Link, brochure entitled *Wirbelsäulen-Chirurgie: Instrumentation Und Implantate Zur Wirbelsäulen-Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77-86, © 1990 Raven Press, Ltd., New York.

Richard W. Porter, MD, FRCS, FRCSE, *Spinal Stenosis and Neurogenic Claudication*, SPINE vol. 21, No. 17, pp. 2046-2052, © 1996, Lippincott-Raven Publishers.

International Search Report for PCT/US06/10521 mailed on Nov. 22, 2006, 7 pages.

* cited by examiner

SYSTEM AND METHOD FOR IMMOBILIZING ADJACENT SPINOUS PROCESSES

PRIORITY CLAIM

This application claims priority to the following U.S. Provisional Patent Application:

U.S. Provisional Patent Application No. 60/446,868, entitled "A System and Method for Immobilizing Adjacent Spinous Processes,", filed Feb. 12, 2003.

CROSS-REFERENCED CASES

The following U.S. Patent Applications are cross-referenced and incorporated herein by reference:

U.S. patent application Ser. No. 09/829,321, entitled "SPINE FIXATION DEVICE AND METHOD" by David Yun, filed Apr. 9, 2001;

U.S. Provisional Patent Application No. 60/421,921, entitled "INTERSPINOUS PROCESS APPARATUS AND METHOD WITH A SELECTABLY EXPANDABLE SPACER" by James F. Zucherman, Ken Y. Hsu, and Charles J. Winslow, filed Oct. 29, 2002;

U.S. patent application Ser. No. 09/579,039, entitled SUPPLEMENTAL SPINE FIXATION DEVICE AND METHOD by James F. Zucherman, Ken Y. Hsu, Charles J. Winslow and Henry A. Klyce, filed May 26, 2000;

U.S. patent application Ser. No. 09/842,819, entitled SUPPLEMENTAL SPINE FIXATION DEVICE AND METHOD by James F. Zucherman, Ken Y. Hsu, Charles J. Winslow and Henry A. Klyce, filed Apr. 26, 2001;

U.S. patent application Ser. No. 09/982,418, entitled SUPPLEMENTAL SPINE FIXATION DEVICE AND METHOD by James F. Zucherman, Ken Y. Hsu, Charles J. Winslow, Steve Mitchell, Scott Yerby and Henry A. Klyce, filed Oct. 18, 2001;

U.S. Provisional Patent Application No. 60/306,262, entitled SUPPLEMENTAL SPINE FIXATION DEVICE AND METHOD by James F. Zucherman, Ken Y. Hsu, Charles J. Winslow, Steve Mitchell, Scott Yerby and Henry A. Klyce, filed Jul. 18, 2001;

U.S. Provisional Patent Application No. 60/421,915, entitled INTERSPINOUS PROCESS IMPLANT WITH RADIOLUCENT SPACER AND LEAD-IN TISSUE EXPANDER by James F. Zucherman, Ken Y. Hsu, Charles J. Winslow, John Flynn and Steve Mitchell, filed Oct. 29, 2002; and U.S. patent application Ser. No. 10/230,505, entitled DEFLECTABLE SPACER FOR USE AS AN INTERSPINOUS PROCESS IMPLANT AND METHOD by James F. Zucherman, Ken Y. Hsu, Charles J. Winslow and John Flynn, filed Aug. 29, 2002.

TECHNICAL FIELD

The present invention relates to methods and systems for immobilizing adjacent spinous processes which, by way of example only, supplement a primary spine fusion device, such as an interbody fusion device.

BACKGROUND

A common procedure for handling pain associated with degenerative spinal disk disease uses devices for fusing together two or more adjacent vertebral bodies. The procedure is known by a number of terms, one of which is interbody fusion. Interbody fusion can be accomplished through the use of a number of methods and devices known in the art. These methods and devices include screw arrangements, solid bone implant methodologies, and fusion devices which include a cage or other mechanism packed with bone and/or bone growth inducing substances. One or more of the above are implanted between adjacent vertebral bodies in order to fuse the vertebral bodies together, thereby alleviating associated pain.

It can be advantageous to associate with such primary fusion devices and methods, supplemental devices which assist in the fusion process. These supplemental devices assist during the several month period when bone from the adjacent vertebral bodies is growing together through the primary fusion device in order to fuse the adjacent vertebral bodies. During this period it is advantageous to have the vertebral bodies held immobile with respect to each other so that sufficient bone growth can be established.

Such supplemental devices can include hook and rod arrangements, screw arrangements, and a number of other devices which include straps, wires, and bands, all of which are used to immobilize one portion of the spine relative to another. All of these devices generally require extensive surgical procedures in addition to the extensive procedure surrounding the primary fusion implant.

It is advantageous for a device and procedure for supplemental spine fixation to be as simple and easy to perform as possible, and optimally such a device and procedure leaves bone, ligament, and other tissue which comprise and surround the spine intact.

BRIEF DESCRIPTION OF THE DRAWINGS

Further details of embodiments of the present invention are explained with the help of the attached drawings in which.

DETAILED DESCRIPTION

Figure 1:
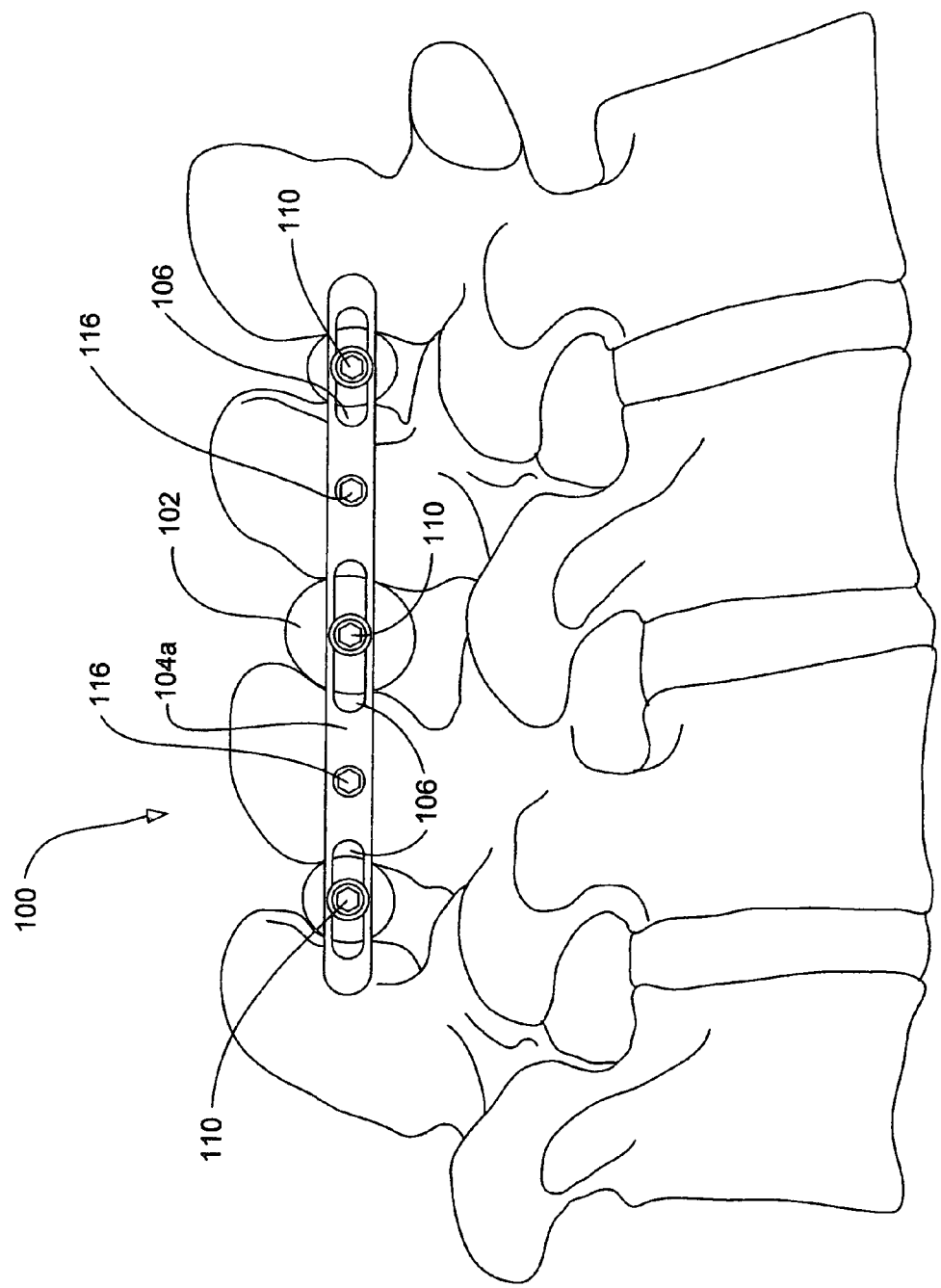
FIG. 1 is a side view of a system in accordance with one embodiment of the present invention positioned about adjacent spinous processes.
Figure 2A:
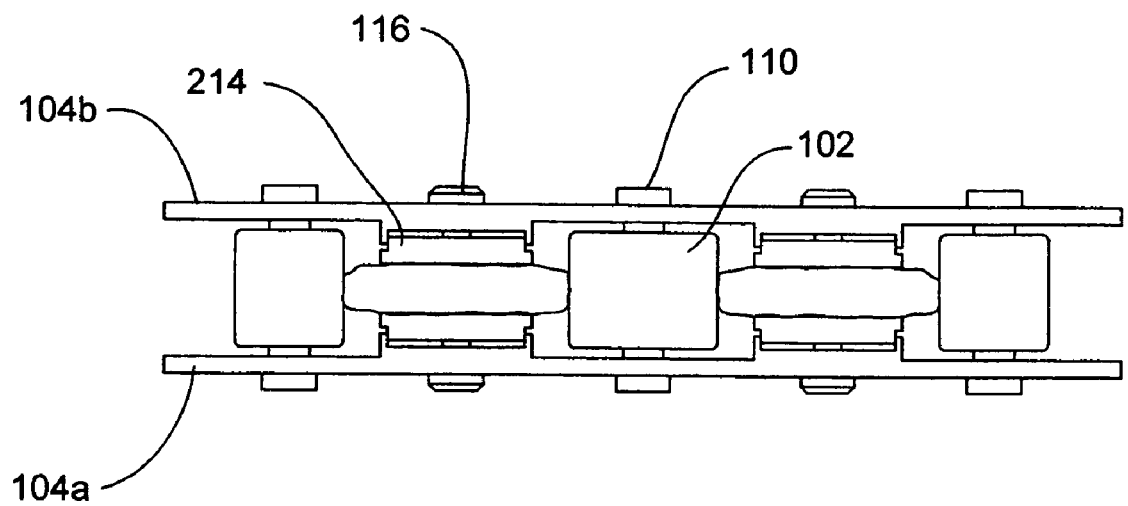
FIG. 2A is a top view of the system shown in FIG. 1.
Figure 2B:
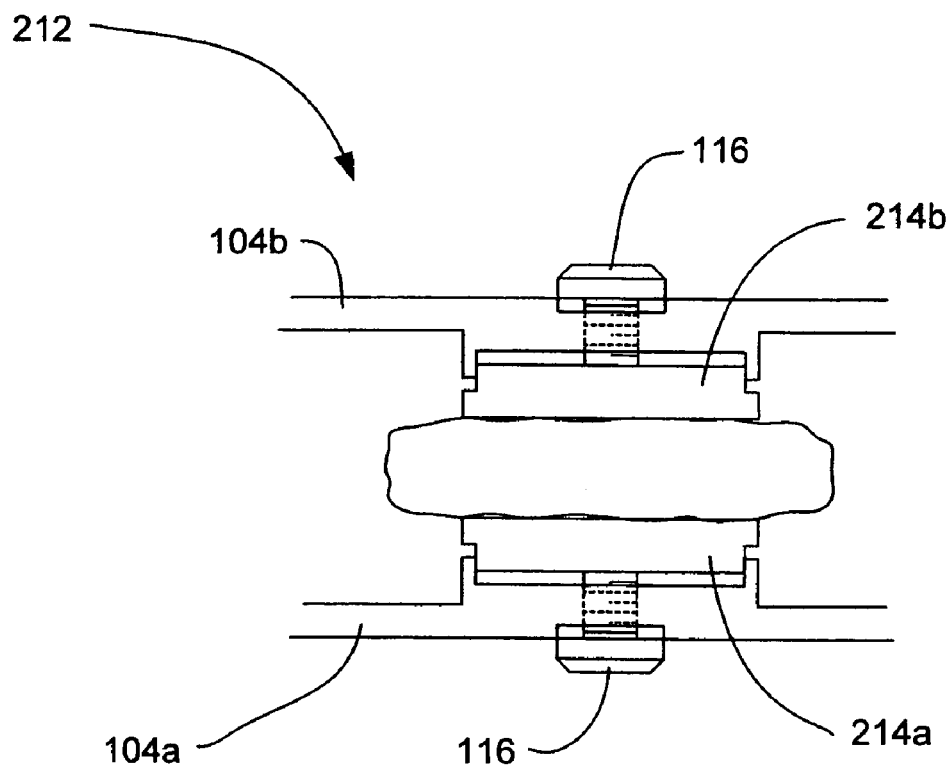
FIG. 2B is a close-up view of two grips positioned on opposite sides of a spinous process as shown in FIG. 2A.

FIGS. 1-2B illustrate a system for immobilizing adjacent spinous processes in accordance with one embodiment of the present invention. The system 100 comprises a scaffold formed by two plates 104a,b adjustably connected by pins 110 inserted through slots 106 in each plate. Each plate 104a,b is positioned generally along a plane parallel to a plane formed by the major axis of the spinous processes, with a first plate 104a positioned on one side of protruding adjacent spinous processes, and a second plate 104b positioned on an opposite side of the adjacent spinous processes, such that the spinous processes are sandwiched between the two plates. Each plate 104*a,b* includes two grips, each grip 214*a,b* comprising part of a clamp adapted for gripping the spinous processes to prevent shifting of the system 100 relative to the spine and to assist in immobilizing the adjacent spinous processes.

As shown in FIG. 2B, a clamp comprises a grip 214*a* from a first plate 104*a* and a grip 214*b* from a second plate 104*b*. The grip 214*a* from the first plate 104*a* is oriented such that the grip substantially opposes a face of a spinous process. The grip 214*b* from the second plate 104*b* is oriented such that the grip substantially opposes the opposite face of the spinous process. The grips 214*a,b* are spaced along the length of the plates 104*a,b* such that each pair of grips 214*a,b* is positioned about a spinous process. In other embodiments, and in the same way that spacers 102 are moveable in slots 106, the grips 214*a,b* can be moveably connected to grip slots in the plates 104*a,b*, thereby allowing each grip 214*a,b* to be moved laterally relative to every other grip 214*a,b*, thus allowing each grip 214*a,b* to be substantially centered with respect to an associated spinous process.

Each grip 214*a,b* is adjustably connected with an associated plate 104*a,b* by a threaded bolt 116 having preferably a hexagonal head for engaging the bolt 116. Twisting the threaded bolt 116 in a first direction drives the bolt 116, and consequently the grip 214*a,b*, toward the spinous process. Twisting the threaded bolt 116 in a direction opposite the first direction drives the grip 214*a,b* away from the spinous process. In other embodiments, the grip 214*a,b* can be connected to the plate 104*a,b* by a slotted screw. In still other embodiments, the grip 214*a,b* can be connected to the plate 104*a,b* by a socketed screw. One of ordinary skill in the art can appreciate the myriad of different fasteners that can be used to adjustably connect each grip 214*a,b* with an associated plate 104*a,b*.

The bolts 116 are provided through a threaded bore in the plates 104*a,b*. Turning the bolts 116 moves the bolts and the grips 214*a,b* secured thereto relative to the plates 104*a,b*. The ends of the bolts 116 can be either fixedly or rotatably secured to the grips 214*a,b*. The bolts 116 can be rotatably secured to the grips 214*a,b* as is know in the art. For example, the ends of the bolts can include a circumferential lip that is received in an undercut groove in a bore of the grips 214*a,b*. The lip is free to rotate in the groove of the bore. Where the bolts 116 are fixedly secured to the grips 214*a,b*, the grips 214*a,b* are preferably circular in cross-section (as the bolts 116 are tightened, the grips 214*a,b* rotate relative to the plates 104*a,b* and thus relative to the spinous processes). One of ordinary skill in the art can appreciate the different means for adjustably connecting the grip 214*a,b* with the plate 104*a,b*.

The plates 104*a,b* and threaded bolts 116 can be made of stainless steel, titanium, and/or other biologically acceptable material such as polyetheretherketone (PEEK). In one embodiment, the grips 214*a,b* can similarly be comprised of a biologically acceptable material such as stainless steel, titanium, and/or other material such as PEEK, with the surface that comes into contact with the spinous process having a roughened or uneven surface. The contacting surface can, for example, be knurled or it can contain spikes to allow the grips 214*a,b* to engage the bone of the spinous processes. In other embodiments, the grips 214*a,b* can be comprised of silicon or other biologically acceptable polymer or material (such as presented below with respect to the spacers). The material can be somewhat deformable and can conform to the surface of the spinous processes.

As shown in FIGS. 1 and 2A, the system 100 has a single clamp positioned at each of two spinous processes, each clamp being comprised of two grips 214*a,b* on opposite sides of an associated spinous process. However, in other embodiments, a plurality of clamps (with associated grips 214*a,b*) can be positioned at selected spinous processes. Thus, for each surface of each spinous process there can be two or more grips. With several grips, each grip can be tightened against a portion of the surface of a spinous process independently of the other adjacent grip that is tightened against a different portion of the same surface of the spinous process. This system can accordingly accommodate uneven surfaces of the spinous processes with each grip tightened against a portion of a surface of a spinous process that is not even with another portion of the surface of the spinous process.

Referring again to FIG. 1, the plates 104*a,b* are secured together with pins 110. A pin 110 can have a threaded bore for receiving a screw or bolt having a hexagonal, slotted, or other type of head at each end of the pin 110. Alternatively, one or both ends of the pin 110 can be threaded for receiving a nut, or lug for example, or other fastener. The pin 110 can be made of a material similar to the plates 104*a,b*, for example, the pin 110 can be made of stainless steel, titanium or other biologically acceptable material. At least one fastener for each pin 110 is tightened so that the pins pull the plates 104*a,b* toward one another as desired. Alternatively, the pins 110 can have a main body diameter thicker than the height of a slot 106 with a thinner threaded end for passing through the slot, thereby predefining a space between plates 104*a,b*.

The clamps are adjusted as desired either before or after the fastener(s) of the pins 110 are tightened, thereby allowing the clamps to grip the spinous processes, making the system 100 rigid. A spacer 102 is moveably and rotatably connected with each pin 110 between plates 104*a,b*. The spacer 102 is substantially cylindrical in shape with an elliptical cross-section sized to conform to a gap between spinous processes in which the spacer 102 is to be inserted. The elliptical spacer 102 has opposite, slightly curved (or relatively flat) surfaces that can distribute the load placed on the spacer by the spinous processes between which the spacer 102 is positioned. The spacer 102 further has curved ends connecting the slightly curved surfaces. The curved ends point substantially posteriorly and anteriorly. The anteriorly pointing ends approach the spine. In other embodiments the spacer 102 can have an egg-shaped cross-section with the curved end pointing toward the spine being smaller that the curved end pointing posteriorly in order to allow the spacer 102 to more closely approach the spine. In still other embodiments, the spacer 102 can have a cross-section having an ovoid, oval or even spherical shape, for example. One of ordinary skill in the art can appreciate the different cross-sectional shapes with which the spacer 102 can be formed in order to distribute load within the spacer 102.

One advantage of using the spacer 102 depicted in FIG. 1 is that the spacer 102 can be partially rotated and repositioned with respect to the system 100 in order to optimize positioning of the spacer 102 between spinous processes. The system 100 is thus designed to account for the various spine structures found in patients. Without having to remove bone from the spine or make multiple adjustments to a hardware system, the spacers 102 and also the grips 214*a,b* allow the system 100 to easily conform to the structure of an associated spine. Further, ease of use and placement allow procedures for implanting the system 100 to be carried out more quickly and with less potential trauma to the surgical site. Still further, as indicated above, the spacers 102 can be located closer to the spine where the bone is stronger, thus affording maximum load bearing and stabilizing support relative to the spine. Such load bearing and stabilizing support is advantageous when the system 100 is used as an adjunct to the fusion of adjacent vertebral bodies. It is to be understood that the cortical bone or the outer bone of the spinous processes is stronger at an anterior position adjacent to the vertebral bodies of the vertebra than at a posterior position distally located from the vertebral bodies.

Still further, for load bearing it is advantageous for the spacer 102 to be close to the vertebral bodies. In order to facilitate this and to accommodate the anatomical form of the bone structures, the spacer 102 rotates relative to the system 100 as the spacer 102 is inserted between the spinous processes and/or urged toward the vertebral bodies so that the spacer 102 is optimally positioned between the spinous processes and the system 100 is optimally positioned relative to the spinous processes. The shape of the spacer 102 is designed so that it conforms to the area that the spacer 102 is inserted into. However, one of ordinary skill in the art will appreciate that the spacer 102 is not limited to having an elliptical cross-section. For example, the spacer 102 can be substantially spherical in cross-section or egg shaped as set forth above.

As can be seen in FIG. 1, the spacers 102 can be of various sizes. Thus for example, using imaging prior to surgery, the anatomy of the individual patient can be determined and the system 100 assembled to suit the particular patient. Additionally, during surgery the physician can be provided with a kit having different sized spacers 102 and the physician can assemble the system 100 with appropriately sized spacers 102 to fit the anatomy of the patient. In this embodiment the pins 110 can be comprised of rods with threaded bores at each end that receive bolts or screws used to secure the pins between two plates 104a,b with the spacer 102 rotatably mounted on the pins 110.

Figure 3:
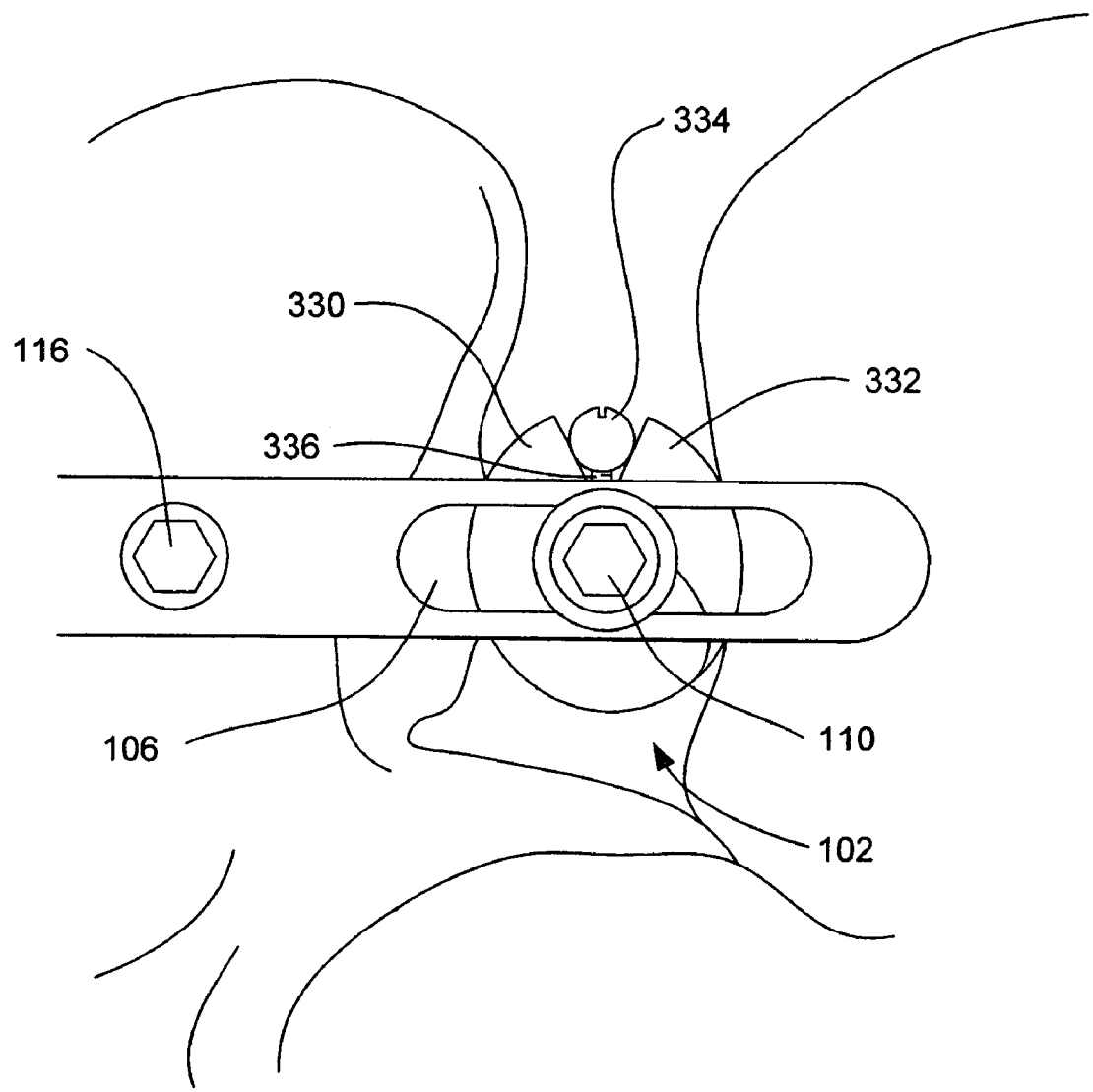
FIG. 3 is a side view of an alternative embodiment of the invention with an expanding spacer.

In other embodiments, the spacer 102 can be comprised of two portions adjustably connected by a hinge to allow expansion of the spacer 102. For example, as shown in FIG. 3, the spacer 102 is comprised of a first portion 330 and a second portion 332 that together have a minor dimension that can be adjusted by rotating a ball 334 connected with a lead screw 336, such that the ball 334 alternatively forces the minor dimension to expand or allows the minor dimension to collapse. Such a spacer is described in pending U.S. Patent Application No. 60/421,921, entitled "INTERSPINOUS PROCESS APPARATUS AND METHOD WITH A SELECTABLY EXPANDABLE SPACER" by James F. Zucherman, Ken Y. Hsu, and Charles J. Winslow, incorporated herein by reference.

The spacer 102 can be made of a polymer, such as a thermoplastic, and can be formed by extrusion, injection, compression molding and/or machining techniques. Specifically, the spacer 102 can be made of a polyketone such as PEEK. One type of PEEK is PEEK 450G, which is an unfilled PEEK approved for medical implantation available from Victrex of Lancashire, Great Britain. Other sources of this material include Gharda located in Panoli, India. PEEK 450G has appropriate physical and mechanical properties and is suitable for carrying and spreading the physical load between the spinous process. For example in this embodiment the PEEK has the following approximate properties:

| | |
|---|---|
| Density | 1.3 g/cc |
| Rockwell M | 99 |

-continued

| | |
|---|---|
| Rockwell R | 126 |
| Tensile Strength | 97 |
| MPa Modulus of Elasticity | 3.5 GPa |
| Flexural Modulus | 4.1 Gpa |

It should be noted that the material selected may also be filled. For example, other grades of PEEK available and contemplated include 30% glass-filled or 30% carbon-filled PEEK, provided such materials are cleared for use in implantable devices by the FDA or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

As can be appreciated, other suitable biologically acceptable thermoplastic or thermoplastic polycondensate materials that resist fatigue, have good memory, are flexible and/or deflectable, have very low moisture absorption and have good wear and/or abrasion resistance, can be used without departing from the scope of the invention. Other materials that can be used include polyetherketoneketone (PEKK), polyetherketone (PEK), polyetherketoneetherketoneketone (PEKEKK), and polyetheretherketoneketone (PEEKK), and generally a polyaryletheretherketone. Further, other polyketones can be used, as well as other thermoplastics. Still further, silicon can also be used or the spacer can be made of titanium and/or stainless steel.

Reference to appropriate polymers that can be used in the spacer can be made to the following documents, all of which are incorporated herein by reference: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials. Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

As mentioned above, each spacer 102 can be connected with a pin 110 that adjustably connects the first plate 104a with the second plate 104b. In one embodiment, each plate 104a,b has three slots 106 spaced and sized such that the slots 106 span approximately the width of the gap between the associated adjacent spinous processes when a patient is standing up. The length of the slots 106 should allow for necessary adjustment of the spacers 102 so that the anatomy of the adjacent spinous processes can be accommodated with the spinous processes immobilized between the spacers 102. In the system 100 shown in FIG. 1, the middle of three slots 106 is sized larger than the slots 106 on either end of the plates. However, in other embodiments, the slots 106 can be sized relative to one another based on the vertebral bodies that are intended to be immobilized.

Figure 4A:
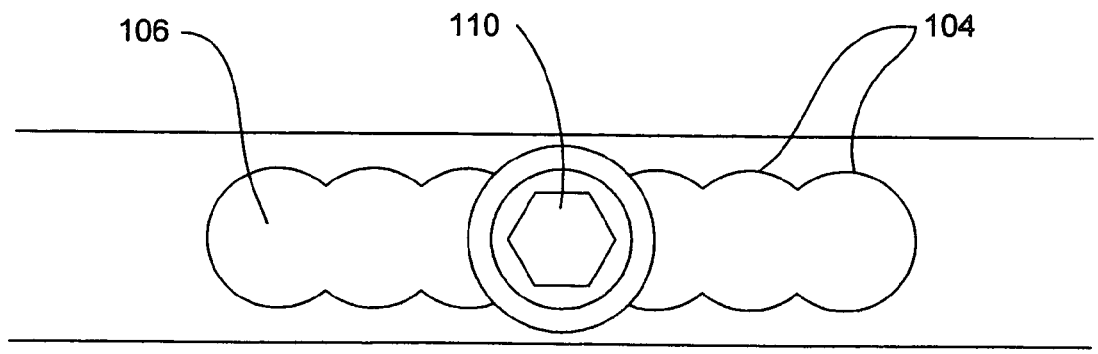
FIG. 4A is a side view of an alternative embodiment of the invention with a slot for positioning a pin having lobed cut-outs.
Figure 4B:
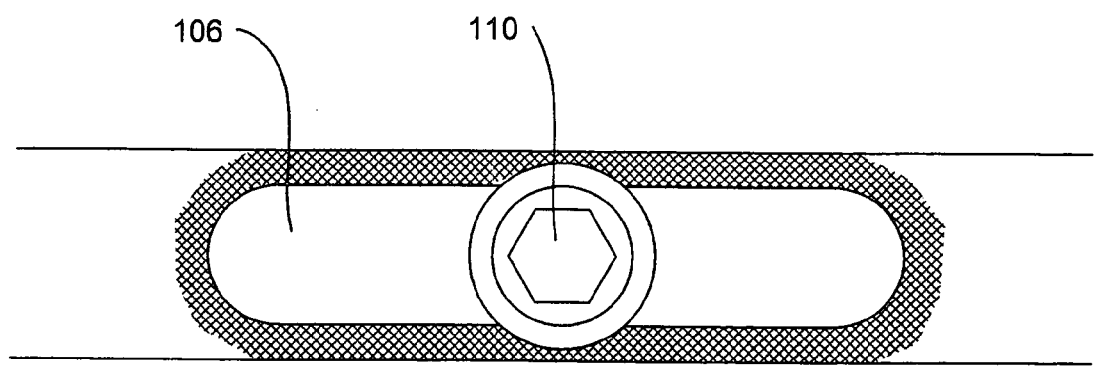
FIG. 4B is a side view of an alternative embodiment of the invention with a slot for positioning a pin having a knurled periphery.

As described above, a pin 110 can be fitted into a slot 106 in each plate 104a,b. The width of the slot 106 allows the pin 110 to be optimally positioned within the gap between spinous processes, while still being fixable to the plates 104a,b. The pin 110 can be fixedly connected with each plate 104a,b by a bolt, screw, nut or other fastener, optionally coupled with a washer. To prevent the plates 104a,b and pins 110 from slipping and shifting relative to one another, a number of different type of slots can be employed to fix the pin 110 in position. As shown in FIG. 4A, one type of slot 106 that can be used is a slot having cut-outs, lobes, or scallops 440 sized such that the cut-outs, lobes or scallops 440 have diameters slightly larger than the diameter of the pin 110, but are separated such that the adjacent cut-outs, lobes, or scallops are joined at a space narrower than the diameter of the pin 110 so that the pin 110 is prevented from sliding to the adjacent position. Another type of slot 106, shown in FIG. 4B, includes knurls around each slot's periphery, intended to be used with a knurled washer placed between a fastener and a plate 104a,b. The knurls on the respective surfaces grip each other when the fastener is tightened, preventing the pin 110 from moving in the slot 106. One of ordinary skill in the art can appreciate the different means for fixing a pin 110 in a slot 106 to prevent the pin 110 from moving relative to the plate 104a,b.

Figure 5:
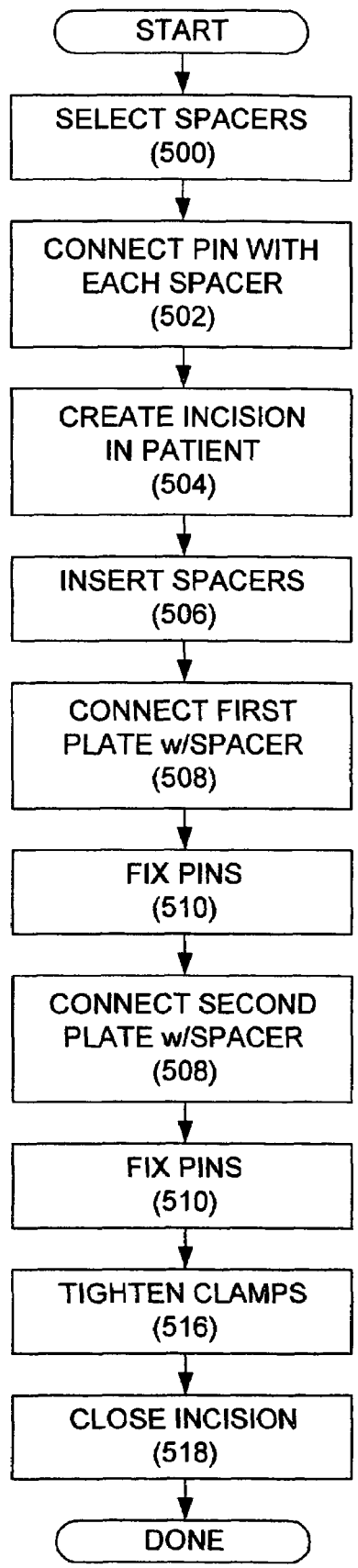
FIG. 5 is a representation of a method for immobilizing adjacent spinous processes in accordance with one embodiment of the present invention.

In alternative embodiments, the system 100 can comprise one or two plates 104a,b with spacers 102 rotatably secured thereto (foregoing the use of grips). The system 100 can be implanted and the position of the spacers 102 can be adjusted relative to the slots 106, the one or two plates 104a,b, and the spinous processes in order to immobilize the spinous processes FIG. 5 is a block diagram showing steps for performing a method for inserting a system 100 into a patient in order to immobilize vertebral bodies in accordance with the present invention. As shown in first block 500, a first, second and third spacer 102 is selected according to the size of the gap between spinous processes that each spacer 102 will occupy. Each spacer 102 is moveably connected with an associated pin 110 (step 502). An incision is made in the patient proximate to vertebral bodies to be immobilized (step 504), and the spinous processes and surrounding tissues are exposed. Each spacer 102 is then inserted into position between targeted spinous processes (step 506) and allowed to rotate and adjust to conform as closely as possible to the contours of the space. A first plate 104a is inserted into the patient and positioned such that a first end of each pin 110 fits into a slot 106 (step 508). Each pin 110 is fixedly connected to the first plate 104a by a fastener, for example a bolt or slotted screw (step 510). A second plate 104b is inserted into the patient and positioned such that a second end of each pin 110 fits into a slot 106 (step 512). Each pin 110 is fixedly connected to the second plate 104b by a fastener, for example a bolt or slotted screw (step 514). Finally, the grips 214a,b are incrementally tightened so that each clamp grips an associated spinous process (step 516). The incision is closed (step 518).

In other embodiments, a method in accordance with the present invention can be applied where there are more or less than three spacers 102, and/or more or less than two clamps. The configuration of a system 100 will depend on the area intended to be immobilized, and the requirements of the patient.

Other methods of insertion, include having the system 100 fully assembled prior to insertion. For this method, the surgical site is prepared and then the system 100 is pushed down over the ends of the spinous processes until the system 100 rests in a desired location. At this point the grips 214a,b are tightened in place about the spinous processes.

Still alternatively, the system 100 can be partially assembled with the spacers 102 assembled with a first plate 104a. This subassembly is positioned alongside of the spinous processes and the spacers 102 are urged between the adjacent spinous processes. When the spacers 102 are positioned, the second plate 104b is secured to the system 100.

The foregoing description of preferred embodiments of the present invention has been provided for the purposes of illustration and description. It is not intended to be exhaustive or to limit the invention to the precise forms disclosed. Many modifications and variations will be apparent to one of ordinary skill in the relevant arts. The embodiments were chosen and described in order to best explain the principles of the invention and its practical application, thereby enabling others skilled in the art to understand the invention for various embodiments and with various modifications that are suited to the particular use contemplated. Other features, aspects, and objects of the invention can be obtained from a review of the specification, the figures, and the claims. It is intended that the scope of the invention be defined by the claims and their equivalence.

The invention claimed is:

1. A system for immobilizing adjacent spinous processes, comprising:
   a first plate having:
   a first adjustable grip adapted for gripping a first spinous process;
   a second adjustable grip adapted for gripping a second spinous process; a first slot at a first position;
   a second slot at a second position; and
   a third slot at a third position;
   a second plate having:
   a first adjustable grip adapted for gripping the first spinous process; and
   a second adjustable grip adapted for gripping the second spinous process;
   a first slot at a first position;
   a second slot at a second position; and a third slot at a third position;
   a first pin positioned in the first slot of the first plate and the first slot of the second plate, thereby connecting the first plate with the second plate;
   a second pin positioned in the second slot of the first plate and the second slot of the second plate, thereby connecting the first plate with the second plate;
   a third pin positioned in the third slot of the first plate and the third slot of the second plate, thereby connecting the first plate with the second plate;
   a first spacer moveably connected with the first pin;
   a second spacer moveably connected with the second pin; and
   a third spacer moveably connected with the third pin.

2. The system for immobilizing adjacent spinous processes of claim 1, wherein each of the adjustable grips is adapted to be adjusted relative to the spinous process so as to be tightened relative to the spinous processes.

3. The system for immobilizing adjacent spinous processes of claim 2, wherein each of the adjustable grips includes one of a bolt and a slotted screw to adjust the adjustable grip.

4. The system for immobilizing adjacent spinous processes of claim 1, wherein at least on of the first, second and third spacers can be expanded.

5. The system for immobilizing adjacent spinous processes of claim 1, wherein each of the first, second, and third spacers is substantially elliptical in cross-section.

6. The system for immobilizing adjacent spinous processes of claim 1, wherein each of the first, second, and third spacers is adapted to be positioned close to a spine and adjacent to portions of the spinous processes to spread the load placed upon the spacer by the adjacent spinous processes.

7. The system for immobilizing adjacent spinous processes of claim 1 wherein each of the first, second, and third spacers is movably attached to the system so that the spacer can be attached at two or more locations on the system.

8. The system for immobilizing adjacent spinous processes of claim 1, wherein each of the first, second, and third slots in the first plate and the second plate includes a plurality of cut-outs, lobes, or scallops such that pins can be positioned to prevent the pins from slipping within the slots.

9. The system for immobilizing adjacent spinous processes of claim 1, wherein knurls are associated with each of the first, second, and third slots in the first plate and the second plate prevent the pins from slipping within the slot.

10. The system of for immobilizing adjacent spinous processes of claim 1, wherein: the first spacer is rotatably mounted on the first pin;

the second spacer is rotatably mounted on the second pin; and the third spacer is rotatably mounted on the third pin.

* * * * *